(12) United States Patent
Bruder et al.

(10) Patent No.: US 9,495,769 B2
(45) Date of Patent: Nov. 15, 2016

(54) CT IMAGE RECONSTRUCTION IN THE EXTENDED FIELD OF VIEW

(71) Applicants: Herbert Bruder, Hoechstadt (DE); Harald Schöndube, Erlangen (DE)

(72) Inventors: Herbert Bruder, Hoechstadt (DE); Harald Schöndube, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 183 days.

(21) Appl. No.: 13/869,081

(22) Filed: Apr. 24, 2013

(65) Prior Publication Data

US 2013/0301894 A1    Nov. 14, 2013

(30) Foreign Application Priority Data

May 8, 2012   (DE) .................. 10 2012 207 629

(51) Int. Cl.
*G06T 11/00* (2006.01)
*A61B 6/00* (2006.01)

(52) U.S. Cl.
CPC .......... *G06T 11/003* (2013.01); *G06T 11/005* (2013.01); *G06T 11/006* (2013.01); *A61B 6/507* (2013.01); *G06T 2211/432* (2013.01)

(58) Field of Classification Search
CPC .............. G06T 7/0012; G06T 11/005; G06T 2211/432; A61B 6/032; A61B 6/4441; A61B 6/027; A61B 6/037
See application file for complete search history.

(56) References Cited

U.S. PATENT DOCUMENTS

| | | | | |
|---|---|---|---|---|
| 4,550,371 A | * | 10/1985 | Glover | G06T 11/005 378/19 |
| 8,503,750 B2 | * | 8/2013 | Benson | A61B 6/5258 378/4 |

(Continued)

FOREIGN PATENT DOCUMENTS

| | | |
|---|---|---|
| CN | 101271574 A | 9/2008 |
| CN | 101408979 A | 4/2009 |

(Continued)

OTHER PUBLICATIONS

Kolditz et al., Comparison of extended field-of-view reconstructions in C-arm flat-detector CT using patient size, shape or attenuation information, Nov. 30, 2011 [retrieved Jun. 18, 2016], Physics in Medicine and Biology, vol. 56, No. 1, pp. 39-56. Retrieved from the Internet: http://iopscience.iop.org/article/10.1088/0031-9155/56/1/003/meta.*

(Continued)

*Primary Examiner* — Matthew Bella
*Assistant Examiner* — Dennis Rosario
(74) *Attorney, Agent, or Firm* — Harness, Dickey & Pierce, P.L.C.

(57) ABSTRACT

A method is disclosed for the reconstruction of image data of an object under examination from measured data, wherein the measured data has been acquired during a relative rotational movement between a radiation source of a computed tomography system and the object under examination. A delimited area between the radiation source and a detector represents a field of view, in respect of which measured data can be acquired. During the measured data acquisition, parts of the object under examination were located at least partly outside of the field of view. A reconstruction is carried out of first image data from the measured data. The first image data is modified via a threshold value comparison, and the modified data is processed with a morphological filter, and projection data is calculated. The measured data is modified using the projection data, and, second image data is reconstructed.

18 Claims, 4 Drawing Sheets

(56) References Cited

U.S. PATENT DOCUMENTS

| | | |
|---|---|---|
| 2008/0159610 A1 | 7/2008 | Haas |
| 2009/0201291 A1* | 8/2009 | Ziv et al. ................ 345/424 |
| 2011/0188723 A1 | 8/2011 | Bruder |

FOREIGN PATENT DOCUMENTS

| | | |
|---|---|---|
| CN | 101576997 A | 11/2009 |
| CN | 102360495 A | 2/2012 |
| DE | 102008003940 A1 | 7/2008 |
| DE | 102010006585 A1 | 8/2011 |

OTHER PUBLICATIONS

H. Bruder, C. Suess, K. Stierstorfer; Efficient Extended Field of View (eFOV) REconstruction Techniques for Multi-Slice Helical CT: Physics of Medical Imaging, SPIE Medical Imaging, Proceedings 2008, vol. 9, No. 30, E2-13; 2008; DE.

Zou, Xiao-Bing et al. "Rebinned BPF reconstruction for helical cone-beam CT with half-cover scanning" Optics and Precision Engineering, vol. 18, No. 9, 2010; 2010.

Chinese Office Action and English translation thereof dated Jul. 24, 2015.

Chinese Office Action and English translation thereof dated Mar. 9, 2016.

* cited by examiner

CT IMAGE RECONSTRUCTION IN THE EXTENDED FIELD OF VIEW

PRIORITY STATEMENT

The present application hereby claims priority under 35 U.S.C. §119 to European patent application number DE 102012207629.8 filed May 8, 2012, the entire contents of which are hereby incorporated herein by reference.

FIELD

At least one embodiment of the invention generally relates to a method for the reconstruction of image data of an object under examination from measured data, wherein the measured data has been acquired from a computed tomography system and, during the measurement, parts of the object under examination were at least partially outside the field of view.

BACKGROUND

Tomographic imaging methods are characterized in that internal structures of an object under examination can be examined without invasive procedures thereby needing to be conducted. One possible type of tomographic image generation consists of taking a number of projections of the object to be examined from different angles. From these projections a two-dimensional sectional image or a three-dimensional volume image of the object under examination can be calculated.

An example of such a tomographic imaging method is computed tomography. There are a multiplicity of methods known for the scanning of an object under examination with a CT system. For example, circular scanning, sequential circular scanning with the object being moved forward, or spiral scanning are used. Other types of scanning which are not based on circular movements are also possible, such as, for example, scans with linear segments. With the aid of at least one x-ray source and at least one detector located opposite, absorption data from the object under examination is taken from different recording angles, and this absorption data or, respectively, projections gathered in this way are calculated by means of appropriate reconstruction methods such as to form sectional images through the object under examination.

For the reconstruction of computed tomographic images from x-ray-CT data records of a computed tomography device (CT device), i.e. from the projections acquired, use is nowadays made, as a standard method, of what is referred to as filtered back projection (FBP). After the acquisition of the data, it is usual for what is referred to as a "rebinning" step to be carried out, in which the data produced from the fan-shaped beam propagating from the source is re-arranged in such a way that it is present in a form as if the detector were to be impinged by x-ray beams running parallel to the detector. The data is then transformed into the frequency range. A filtering process takes place in the frequency range, and the filtered data is then transformed back. With the aid of the thus resorted and filtered data, a back projection onto the individual voxels then takes place within the volume of interest. However, due to their approximative mode of operation, problems arise with the traditional FBP methods with what are referred to as low-frequency cone-beam artifacts and spiral artifacts. In addition to this, with traditional FBP methods the sharpness of the image is linked to the image noise. The higher the sharpness achieved, the higher also the image noise, and vice-versa.

The FBP method belongs to the group of approximative reconstruction methods. There also exists the group of exact reconstruction methods, but at the present time these are scarcely used. Finally, a third group of reconstruction methods is formed by the iterative methods.

Due to the expansion of the detector, there is a limited measuring range available, the field of view. This means that, at a specific projection angle, projection data or measured data can be acquired only for those volume elements of an object under examination which lie within the field of view. The problem frequently arises, however, that the expansion of the object under examination is of such a nature that not all the parts of the object under examination are located inside the field of view during the entire period of measured data acquisition. This leads to incomplete measured data records with regard to these parts of the object under examination, and therefore to artifacts during the image reconstruction.

SUMMARY

At least one embodiment of the invention discloses a method for the reconstruction of CT images from measured data, wherein account is intended to be taken of the fact that the object under examination exceeds the field of view. In addition, a corresponding control and calculation unit, a CT system, a computer program, and a computer program product are also to be disclosed.

A method, a calculation unit, a CT system, a computer program, and a data carrier with features from dependent claims are disclosed. Advantageous embodiments and further developments form the subject matter of the subclaims.

With the method according to at least one embodiment of the invention for the reconstruction of image data of an object under examination from measured data, the measured data was initially acquired during a relative rotational movement between a radiation source of a computed tomography system and the object under examination. In this situation, a delimited area between the radiation source and a detector represents a field of view, in respect of which measured data can be acquired. During the acquisition of the measured data, parts of the object under examination were located at least at certain times outside the field of view. A reconstruction takes place of first image data from the measured data. The first image data is modified by way of a threshold value comparison. The modified first image data is processed with a morphological filter, and projection data is calculated from the modified first image data processed in this way. Next, the measured data is modified by making use of the projection data. From the modified measured data, second image data is reconstructed.

The CT system according to at least one embodiment of the invention comprises such a calculation unit. It may also contain other constituent parts, which are required, for example, for the acquisition of measured data.

The computer program according to at least one embodiment of the invention is provided with program code, which has the effect of carrying out a method of the described type when the computer program is run on a computer.

The data carrier according to at least one embodiment of the invention, which is readable by a computer, stores program code of a computer program, which has the effect of carrying out a method of the type described when the computer program is run on a computer.

BRIEF DESCRIPTION OF THE DRAWINGS

The invention is described hereinafter on the basis of an example embodiment. In this situation, the figures show.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

With the method according to at least one embodiment of the invention for the reconstruction of image data of an object under examination from measured data, the measured data was initially acquired during a relative rotational movement between a radiation source of a computed tomography system and the object under examination. In this situation, a delimited area between the radiation source and a detector represents a field of view, in respect of which measured data can be acquired. During the acquisition of the measured data, parts of the object under examination were located at least at certain times outside the field of view. A reconstruction takes place of first image data from the measured data. The first image data is modified by way of a threshold value comparison. The modified first image data is processed with a morphological filter, and projection data is calculated from the modified first image data processed in this way. Next, the measured data is modified by making use of the projection data. From the modified measured data, second image data is reconstructed.

The object under examination is too large for the field of view of the CT device. This means that, depending on the projection angle, in other words, depending on the position of the x-ray source relative to the object under examination, more or less large constituent parts of the object under examination do not lie within the field of view, with the result that no data acquisition can take place for the respective projection angle in respect of these constituent parts. Accordingly, for some volume elements of the object under examination there is an incomplete measured data record available. This incompleteness of the measured data leads to artifacts, even for those constituent parts of the object under examination which were in the field of view throughout the entire data acquisition. In order to reduce the undesirable effect on the images which are being reconstructed, due to the incompleteness of the measured data incurred by the measured field being exceeded, according to the invention there is not only a single image reconstruction carried out, but a two-fold reconstruction.

The first image data is modified and then subjected to a morphological filtering process. This encompasses, for example, a closing operation. Due to the morphological filter, the modified first image data is manipulated, such that it exhibits advantageous properties in relation to the calculation of the second image data. In particular, morphological filters make it possible for jagged object delimitations which are present in the modified first image data to be eliminated or at least partially smoothed.

The morphological filter is not applied directly onto the first image data, but only after this has been modified by making use of a threshold value comparison. This modification preferably only affects a part quantity of the first image data; a repeat processing of the entire first image data is however also possible.

Next, the modified and filtered first image data is used to calculate projection data. The projection data represents artificial or calculated measured data; it may therefore be derived from this to which measured data a hypothetical CT recording of an object corresponding to the modified and filtered first image data would lead. While it is possible to pass from the measured and projection data to the image data by way of an image reconstruction algorithm, a forwards projection of the image data leads to the projection data.

The projection data is used to modify the measured data. In the simplest case, the modification can correspond to a supplementing of the measured data, such that the incompleteness of the measured data, which is based on the field of view being exceeded, will be alleviated. It is further possible that, in addition or as an alternative to the supplementing, a change in the measured data is also carried out.

The modified measured data is then used as a basis for an image reconstruction. The resulting second image data is better than the first image data, since it is not based on the original measured data but on the modified measured data. This data already contains findings relating to the delimitation of the object under examination, which correspond to the processing of the first image data.

In a further embodiment of the invention, during the modification of the first image data, pixel values of pixels are assigned with a first or second pixel value, as a function of the comparison with a threshold value. There are accordingly two possibilities for this pixel value allocation assignment: Allocation assignment with the first pixel value or allocation assignment with the second pixel value. Which of the two pixel values is used depends on the threshold value comparison; since only one single threshold value is used, the result of the comparison may transpire to be smaller, the same, or larger.

As an alternative to this, it is possible, during the modification of the first image data, for pixel values of pixels to be allocated assigned as a function of the comparison of a plurality of threshold values with a pixel value from a plurality of pixel values made available for this purpose. Accordingly, there exist not only two, but more than two pixel values which are used for the allocation assignment of pixels. By contrast with the binary allocation assignment described heretofore, this allows for an allocation assignment with continuous, or at least with several, pixel values. To do this, use is not only made of one single threshold value, but of a plurality of threshold values. If, for example, two threshold values are used, then the result of the threshold value comparison will be: smaller than the smaller threshold value, equal to the smaller threshold value, between the smaller and the larger threshold value, equal to the larger threshold value, larger than the larger threshold value. It is of course possible for more than two threshold values to be used.

The provision of a plurality of pixel values for the assignment of the first image data makes it possible for the first image data to be approximated to the actual constitution of the object under examination. This is advantageous, since due to the field of view being exceeded, there are errors present in the first image data.

The use of a continuous function for the pixel value assignment is advantageous, wherein this continuous function represents an allocation between in each case a pixel value of the first image data and a pixel value from the plurality of pixel values available. The continuous function therefore indicates with which pixel value a pixel of the first image data is to be allocated/assigned. This does not have to apply to all pixel values, but much rather to a range of pixel values, which are delimited by the threshold values.

After the pixel value allocation, the first image data is subjected to a smoothing filtering process. This makes it possible, beyond the use of the morphological filter, for jagged object edges to be avoided.

It is advantageous if, at the modification of the first image data, exclusively pixel values of pixels are modified which provide images of parts of the object under examination which, during the measured data acquisition, were located at least in partly outside the field of view. It is true that exceeding the field of view also has an effect on the first image data inside the field of view; the aim, however, is for a measured data supplement to be undertaken for the areas outside the field of view, such that the image data of parts of the object under examination, which were at least partially outside the field of view during the measured data acquisition, is particularly relevant.

The modification of the measured data serves to produce a data record which is used as the data to be taken as the basis for the reconstruction of the second image data. As usable values in this context, consideration is given in particular to the original measured data and the projection data.

In a further embodiment of the invention, in the modification of the measured data for at least one area outside the detector, the respective projection data is used as the data for the basis for the reconstruction of the second image data. This corresponds to a supplementing of the measured data.

This is because the measured data could only be acquired by the detector; for areas outside the detector, there is naturally no measured data available. The supplementing therefore makes provision for the situation as if data were also being acquired outside the detector, which can be used for the image reconstruction.

In addition or as an alternative it is possible, at the modification of the measured data, for at least one area of the detector, for the respective measured data to be regarded as the data to be taken as the basis for the reconstruction of the second image data. This means that there are one or more areas inside the detector of which the measured data is not changed. Rather, this data is taken unchanged as the basis for the image reconstruction of the second image data. Particularly well-suited for this is the middle area of the detector. It is also possible, however, for the measured data not to change for the entire detector area, but, in the same manner as for the reconstruction of the first image data, for it to be taken as the basis for the reconstruction of the second image data. This would mean only supplementing the measured data and not changing its values.

In addition or as an alternative it is possible, at the modification of the measured data, for at least one area at the edge of the detector to be regarded as a combination of the respective measured data and the respective projection data, and as the data to be taken as the basis for the reconstruction of the second image data. A combination of this nature is preferentially calculated as a weighted sum. Preferentially, the weighting takes place in such a way that, as the distance from the detector edge increases, the measured data will increase in weight in comparison with the projection data. Suitable as the weighting function is, for example, a cos 2 function.

In a further embodiment of the invention, use is made for the reconstruction of the first image data of a method for image reconstruction in the extended field of view. This involves methods which may already be known per se, and which already take account of the fact that an exceeding of the field of view exists. Such methods lead to better results in the image reconstruction than algorithms, which do not take account of the field of view being exceeded. In this way, use is made, with the first image data as the starting point for the following method, of image data which is already improved in comparison with simple image reconstruction methods.

The calculation unit according to at least one embodiment of the invention serves to reconstruct image data of an object under examination from measured data of a CT system. It exhibits means for carrying out at least one embodiment of the method described. In particular, it may comprise a program memory for storing a program code, wherein, if appropriate, among other items, program code of a computer program is present which is suitable for carrying out at least one embodiment of the method of the type described heretofore, or to cause or control this being carried out, when the computer program is run on a computer. The calculation unit may also be realized by a plurality of facilities connected to one another and located at different places. This corresponds to a distribution of the functionality of the calculation unit over several constituent parts. Advantageously, the calculation unit is additionally in a position to control a measurement procedure of the CT system.

The CT system according to at least one embodiment of the invention comprises such a calculation unit. It may also contain other constituent parts, which are required, for example, for the acquisition of measured data.

The computer program according to at least one embodiment of the invention is provided with program code, which has the effect of carrying out a method of the described type when the computer program is run on a computer.

The data carrier according to at least one embodiment of the invention, which is readable by a computer, stores program code of a computer program, which has the effect of carrying out a method of the type described when the computer program is run on a computer.

Figure 1:
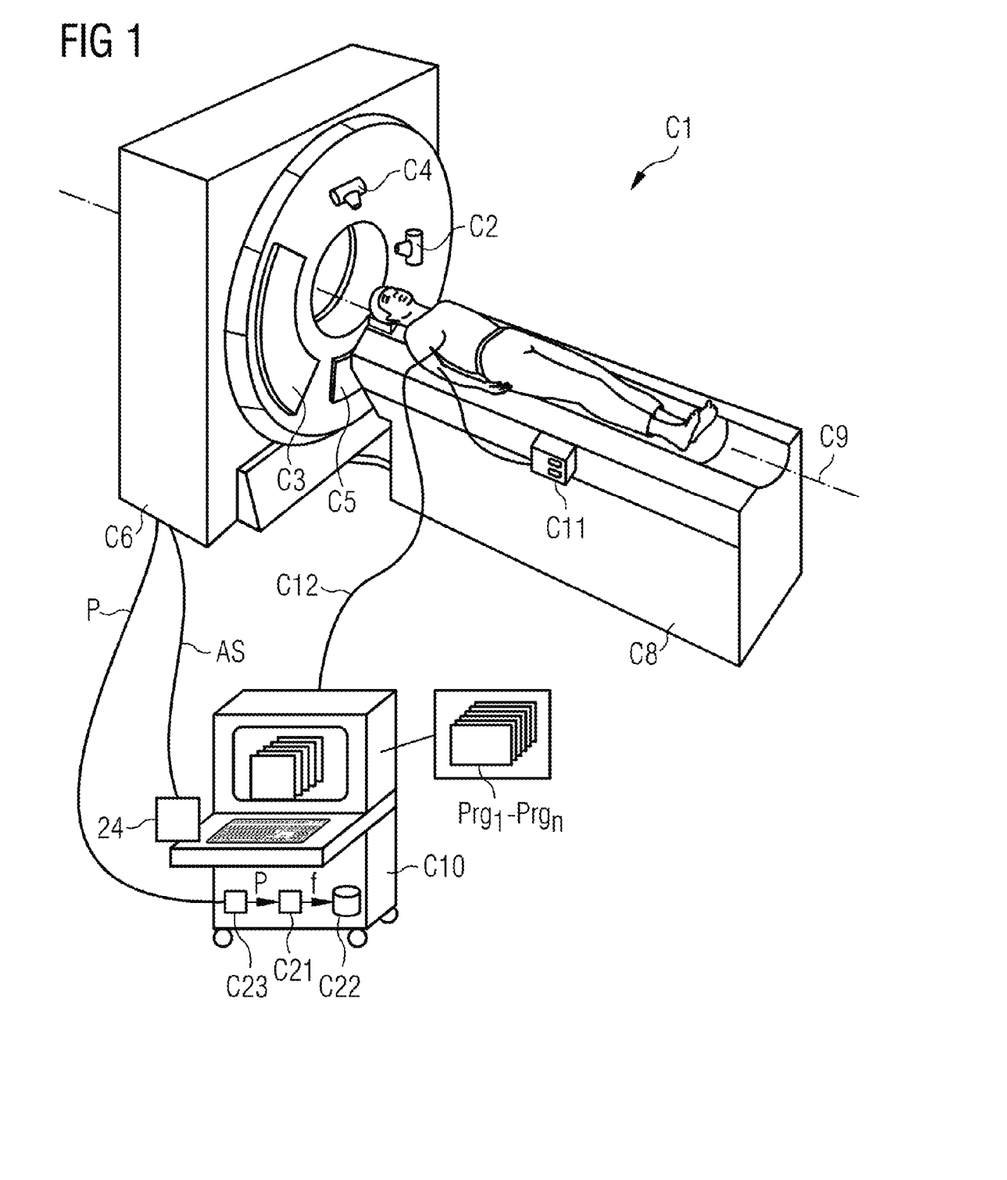
FIG. 1: a first schematic representation of an example embodiment of a computed tomography system with an image reconstruction constituent part.

In FIG. 1, there is first a schematic representation of a first computed tomography system C1 with an image reconstruction facility C21. This relates to a CT device of what is referred to as the third generation, but the invention is nevertheless not restricted to this. Located in the gantry housing C6 is a closed gantry, not visible here, arranged on which are a first x-ray tube C2 with a detector C3 opposite it. As an option in the CT system shown here, a second x-ray tube C4, with a detector C5 located opposite it, is arranged in such a way that, as a result of the radiator/detector combination additionally provided, a higher time resolution can be attained, or, with the use of different x-ray energy spectra in the radiator/detector systems, "dualenergy" examinations can also be carried out.

The CT system C1 is further provided with a patient couch C8, on which a patient can be pushed into the field of view during the examination, along a system axis C9, also designated as the z-axis. It is also possible, however, for the scanning itself to take place as a pure circular scan, without the patient being pushed forward, exclusively in the examination area of interest. The movement of the patient couch C8 relative to the gantry is effected by a suitable motorization. During this movement, in each case the x-ray source C2 and C4 respectively rotate around the patient. The detector C3 and C5 respectively runs in parallel with this, opposite the x-ray source C2 and C4 respectively, in order to acquire projection measured data, which is then used for the reconstruction of sectional images. As an alternative to a sequential scan, in which the patient is pushed step by step through the examination field between the individual scans, there is naturally also the possibility of a spiral scan, with which the patient, during the circumferential scanning with the x-ray radiation, is continuously pushed along the system axis C9 through the examination field between x-ray tubes C2 and C4 respectively and detector C3 and C5 respectively. Due to the movement of the patient along the axis C9 and the simultaneous circumferential movement of the x-ray source C2 and C4 respectively, during a spiral scan, a helical path is produced for the x-ray source C2 and C4 respectively relative to the patient during the measurement. This path can also be achieved by the gantry being pushed along the axis C9 when the patient is stationary. It is also possible for the patient to be moved continuously and, if appropriate, periodically backwards and forwards between two points.

The CT system C1 is controlled by a control and calculation unit C10, with computer program codes Prg1 to Prgn being present in a memory. It is pointed out that these computer program codes Prg1 to Prgn may also be contained on an external storage medium, and, if required, can be loaded into the control and calculation unit C10.

From the control and calculation unit C10, it is possible, via an interface 24, for acquisition control signals AS to be transferred in order to actuate the CT device in accordance with specific measurement protocols. The acquisition control signals AS affect in this case, for example, the x-ray tubes C2 and C4, wherein stipulations may be set with regard to their capacity and the points in time of their being switched on and off, as well as the gantry, wherein stipulations can be set with regard to their rotational speed, as well as to the couch advance movement.

Due to the fact that the control and calculation unit C10 is provided with an input console, measurement parameters can be input by a user or an operator of the CT device, which then controls the data acquisition in the form of acquisition control signals AS. Information about measurement parameters currently being used can be displayed on the screen of the control and calculation unit C10; further information which is relevant for the operator can also be displayed.

The projection measured data p, or raw data respectively, acquired by the detector C3 and C5 respectively, is transferred via a raw data interface C23 to the control and calculation unit C10. This raw data p is then, if appropriate after a suitable pre-processing, further processed in an image reconstruction component C21. In this example embodiment, the image reconstruction component C21 is realized in the control and calculation unit C10 in the form of software on a processor, for example in the form of one or more of the computer program codes Prg1 to Prgn. With regard to the image reconstruction, the principle applies, as already explained with regard to the controlling of the measurement process, that the computer program codes Prg1 to Prgn can also be contained on an external storage medium and, if required, can be loaded into the control and calculation unit C10. It is also possible for the controlling of the measurement process on the one hand, and the image reconstruction on the other, to be carried out by different calculation units.

The image data of reconstructed by the image reconstruction component C21 is then stored in a memory C22 of the control and calculation unit C10 and/or output in the usual way on the screen of the control and calculation unit C10. It may also be fed in via an interface, not represented in FIG. 1, into a network connected to the computed tomography system C1, such as, for example, a radiological information system (RIS), and stored in a mass memory accessible there, or output as images.

The control and calculation unit C10 can additionally also carry out the function of an EKG system, wherein a wire C12 is used to conduct the EKG potentials between the patient and the control and calculation unit C10. In addition, the CT system C1 shown in FIG. 1 is also provided with a contrast medium injector C11, by which additional contrast medium can be injected into the patient's blood circulation, such that, for example, the patient's vessels, in particular the heart chambers of the beating heart, can be better represented. Additionally, this also provides for the possibility of carrying perfusion measurements, for which the proposed method is likewise well suited.

The control and calculation unit C10, unlike that represented in FIG. 1, naturally does not have to be located in the vicinity of the remaining constituent parts of the CT system C1. Instead, it is possible for this to be accommodated in another room, or a location even further away. The transfer of the raw data p and/or the acquisition signals AS and/or the EKG data can be carried out via a wire, or, as an alternative, by radio.

Figure 2:
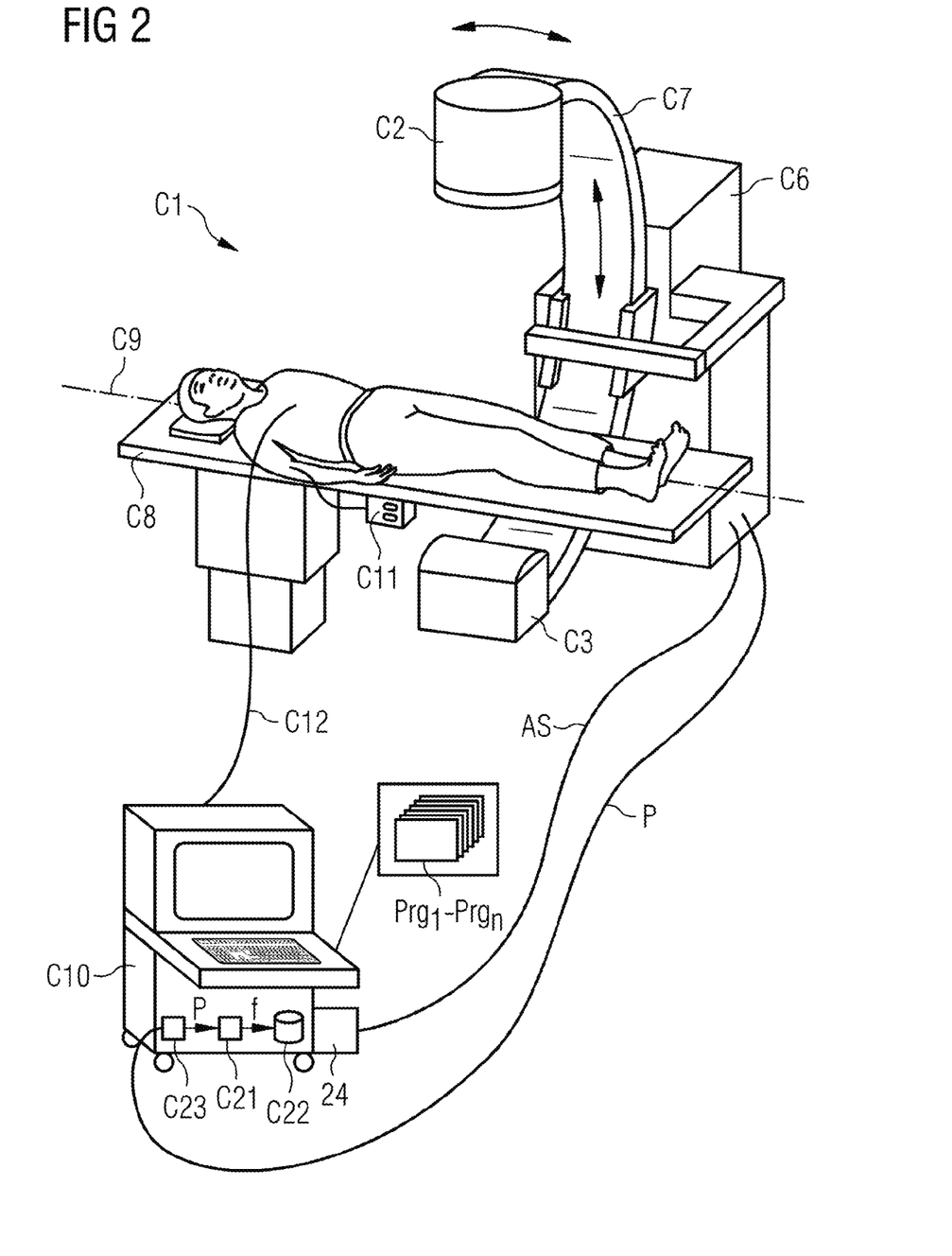
FIG. 2: a second schematic representation of an example embodiment of a computed tomography system with an image reconstruction constituent part.

FIG. 2 shows a C-arm system, with which, by contrast with the CT system from FIG. 1, the housing C6 carries the C-arm C7, secured to which are, on the one hand, the x-ray tubes C2 and, on the other hand, the detector C3 located opposite. For a scanning procedure, the C-arm C7 is likewise pivoted about a system axis C9, such that scanning can take place from a plurality of scanning angles, and corresponding projection data p can be determined from a plurality of projection angles. The C-arm system C1 from FIG. 2, like the CT system from FIG. 1, is provided with a control and calculation unit C10 of the type described in FIG. 1.

An embodiment of the invention can be used in both of the systems shown in FIGS. 1 and 2. Moreover, it can in principle also be used for other CT systems, for example for CT systems with a detector forming a complete ring.

For the image reconstruction, the presence of a complete measured data record is important. "Complete" in this context means that each volume element of the object under examination, which is to be contained in the CT image, must be irradiated over a projection angle range of 180°, if measurement is being carried out in parallel radiation geometry, or of 180° plus the cone aperture angle if the measurement is being carried out in cone-beam geometry, and the corresponding projections must be acquired by the detector. If this cannot be achieved, an image reconstruction is indeed nevertheless still possible, but the resultant image will have artifacts imposed due to the incompleteness of the measured data record.

Figure 3:
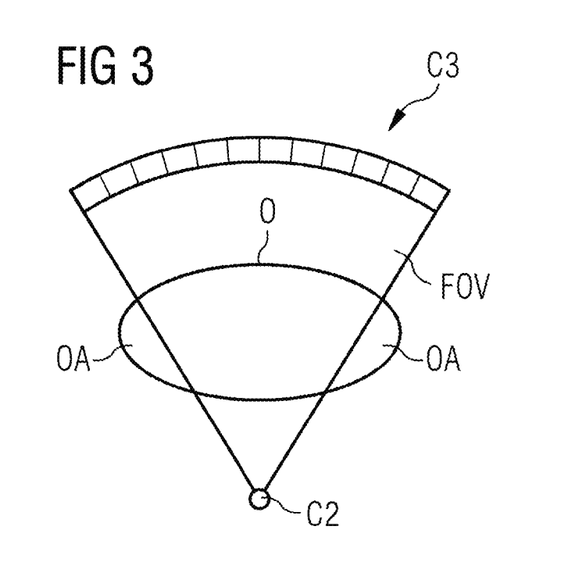
FIG. 3: a section of the recording geometry perpendicular to the z-direction.

Problems arise if the expansion of the object under examination is greater than the field of view of the CT device. Such a situation is represented in FIG. 3. This shows an extract from a CT device according to FIG. 1 or 2, which includes the x-ray source C2 and the detector C3. For the sake of clarity, the detector C3 exhibits in the channel direction only 12 detector elements; in reality, there number is considerably greater. Located between the x-ray source C2 and the detector C3 is the object under examination O. FIG. 3 shows a section perpendicular to the z-axis; what is to be seen is therefore an axial section through the object under examination O. The field of view FOV of the CT device, at a specific projection angle, as shown in FIG. 3, in the section perpendicular to the z-axis, corresponds to a circular section. The edges of this are formed by the x-rays, which pass from the x-ray source C2 to the outermost edges of the detector C3.

It is therefore the expansion of the detector in the channel direction which determines the size of the field of view FOV. The channel direction in this situation is the direction on the detector surface perpendicular to the line direction. The line direction extends perpendicular to the plane of the section in FIG. 3, and therefore along the z-direction. The detector dimension in the plane of the drawing in FIG. 3 is the channel direction.

It can be seen from FIG. 3 that the object under examination O, at the projection angle represented, does not lie fully inside the field of view FOV. The constituent parts OA of the object under examination O, in the position of the x-ray source C2 and the detector C3 according to FIG. 3, are not irradiated by x-rays which are acquired by the detector C3: the constituent parts OA of the object under examination O lie outside the field of view FOV. If the x-ray source C2 and detector C3 rotate about the object under examination O, then, at a number of projection angles, the parts OA of the object under examination O, which in the arrangement according to FIG. 3 lie outside the field of view FOV, then come to lie inside the field of view FOV, while for other projection angles they lie outside the field of view FOV. The same also applies accordingly for the other peripheral areas of the object under examination O.

This means that for a number of constituent parts of the object under examination O no complete measured data record is available. In general, the principle applies that the entire field of view of the CT device, i.e. that area between the x-ray source C2 and detector C3, for which complete data records are being acquired, will be determined by the quantity of sections of the beam fans over a half circuit of the x-ray source C2 and detector C3, or, respectively, over a half circuit of 180° plus the cone aperture angle. The extended field of view of the CT device is an area which connects to the described area of the overall field of view. Outside the overall field of view lies the extended field of view, which comprises those volume elements which are only irradiated by x-ray radiation at some projection angles, and which then pass to the detector.

For constituent parts of the object under examination inside the extended field of view, such as, for example, the parts OA from FIG. 3, this means that in some of the adopted projections, information is contained in the measured data relating to these parts of the object under examination, while in other projections it is not. With regard to the constituent parts of the object under examination, which are located in the extended field of view, there is accordingly an incomplete data record provided. This is also designated as "limited angle" scanning.

An exceeding of the field of view through parts of an object under examination comes about in practice, for example, due to the size of a patient's body, or because a patient, during a thorax measurement, is not able to lay his arms over or behind his head.

Due to the fact that information relating to the object under examination in a number of projections is contained within the extended field of view, it is not possible without further ado to reconstruct a CT image only for the area of the overall field of view. Rather, the exceeding of the field of view leads to a situation in which the CT image inside the overall field of view is affected by artifacts. The reason for this is the incompleteness of the data of the extended field of view as explained heretofore. The information of the extended field of view must therefore be taken into account in the image reconstruction.

There are various different approaches for determining sufficiently good weakening values for the extended field of view. On the one hand it would be possible for the field of view to be extended by enlarging the detector in the channel direction. This approach, however, requires different types of detectors and an adaptation of the gantry, which is cost-intensive and therefore undesirable. On the other hand, there exist software-based approaches for extrapolating projection data in relation to the extended field of view from the measured values. For example, the measured data of the field of view can be reflected into the extended field of view lying outside the field of view, and in this situation is provided with a weighting factor. Depending on the object geometry, the results are not always satisfactory due to the inadequate certainty of the mathematical problem. As a rule, however, with such methods qualitatively satisfactory image values can be obtained at least within the field of view, while the image values outside the field of view are heavily affected by artifacts and are unreliable.

Such a possibility for image reconstruction in the extended field of view is described in the publication by H. Bruder et al: "Efficient Extended Field-of-View (eFOv) Reconstruction Techniques for Multi-Slice Helical CT", Physics of Medical Imaging, SPIE Medical Imaging, Proceedings 2008, Vol. 9, No. 30, E2-13.

Hereinafter use is made of the finding that, with a known object geometry in the extended field of view, very largely correct and stable CT values can be reconstructed. A known object geometry means in this context that the location of the delimitations of the object under examination are known. The procedure with regard to the image reconstruction is explained on the basis of the flow diagram from FIG. 4.

Figure 4:
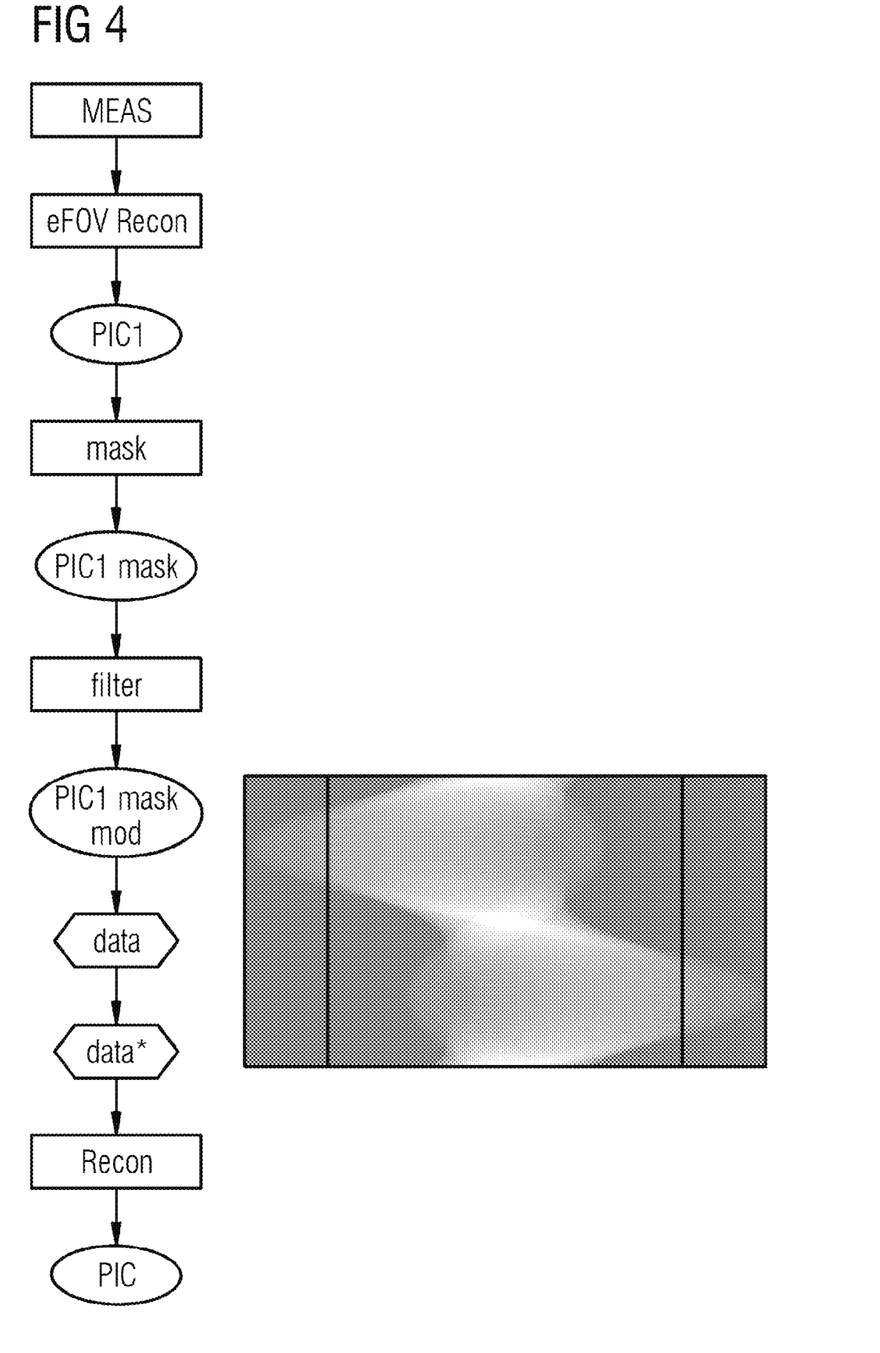
FIG. 4: a flow diagram.

According to the MEAS CT measurement, which can be carried out in a known manner, the measured data $p_{k,s,r}^{meas}$ (the index k stands in this situation for the channel of the detector, the index s for the line of the detector, and the index r for the projection angle). First, this measured data $p_{k,s,r}^{meas}$ is used in the step "eFOV Recon" in order to carry out a conventional image reconstruction in the extended field of view. For this, use may be made, for example, of the method presented in the publication cited above. As a result of the eFOV Recon step there is accordingly a first image PIC1 of the object under examination provided, both inside the overall field of view as well as inside the extended field of view.

In the following step "mask", first this image PIC1 is used in order to determine the contour, i.e. the delimitation of the object under examination. This is carried out on the basis of a threshold value formation, i.e. all the pixels of which the CT values exceed a threshold value are added to the object under examination, and those pixels of which the CT values lie below the threshold value are interpreted as not belonging to the object under examination. As a threshold value, for example, a CT value of −500 HU is suitable, which lies between the HU value of air (−1000 HU) and that of water (0 HU).

Moreover, in the step "mask", all the pixels which according to the threshold value differentiation have been recognized as belonging to the object under examination, and which lie outside the overall field of view and inside the extended field of view, are assigned with a constant CT value. A suitable example is the CT value of water. The CT values of the pixels inside the overall field of view are not changed. As a result of the "mask" step, a modified CT image "PIC1 mask" is therefore provided of the object under examination. This modified image "PIC1 mask" is designated hereinafter as the mask image; in the extended field of view, a mask with the CT value of water was, so to speak, laid over the original image PIC1.

The purpose of using the mask image PIC1 mask is, by means of a forwards projection into the data space and a repeat back projection, to obtain an improved image. The inventors have recognized that the disadvantage in the use of the mask image PIC1 mask is that its edges are jagged, and that, moreover, holes may occur in the mask. Holes in this context are parts of the object inside the extended field of view, which were not occupied by the CT value of water, since they were not identified at the threshold value operation as not belonging to the object. If the object edge is observed, it exhibits in part deep indentations, similar to fjords in an image of a sea coastline.

The reason for the presence of these non-physiological features, i.e. the jagged object borders and the holes, lies in the fact that the image reconstruction eFOV Recon in the extended measurement range does not usually provide any optimum results, with the result that the threshold value operation produces the non-physiological features. The inventors have further recognized that such non-physiological features, if taken as the basis for a data calculation and a consequent image reconstruction, pass wholly or partially into the result image. Accordingly, the attempt is made in the first instance to eliminate the non-physiological features of the mask image PIC1 mask.

In the filter step, a follow-on processing takes place of the mask image PIC1 mask through a morphological Filter. A morphological filter is a non-linear filter; the basic operations are "erosion" and "dilatation". The "opening" is erosion followed by dilatation, and "closing" is dilatation followed by erosion. During these inherently known image processing methods, filtering takes place with the aid of structuring elements. By suitable selection of the parameters of the structuring element, specific image areas can be eliminated or emphasized in relation to others.

Particularly advantageous is the use of a closing filter. This takes effect on the mask image PIC1 mask in such a way that its jagged edges are eliminated, by the protrusions being smoothed out. A smooth object edge is therefore achieved, which corresponds more to the physiological structure. The depressions in the object edges of the mask image PIC1 mask are filled in by the use of the closing filter with the CT value of water.

A similar effect can be achieved by other morphological filters: due to the erosion the depressions at the object edge are enlarged, such that they grow together, as a result of which the object edge is smoothed and pressed inwards. Due to the dilatation, the depressions are closed, with the object edge being pushed outwards. Due to the opening, projecting structures are eliminated.

By the use of a morphological filter in the "filter" step, a modified mask image results, PIC1 mask mod. In comparison with the original mask image PIC1 mask, this corresponds to the situation that the filling out with the CT value of water does not take place along the line threshold value, but along a smoothed line.

Following this, projection value data is calculated from the modified mask image PIC1 mask mod. It is therefore calculated which measured value data would lead to the modified mask image PIC1 mask mod. This artificial measured value data is obtained by a forwards projection, wherein the scan geometry is introduced into this calculation. An example of a scan geometry is a spiral scanning with a multi-line detector.

Data is represented, by way of example in FIG. 4, as well as the artificial measured value data in a sinogram space. The sinogram represents a two-dimensional space per detector line, which is stretched on the one hand by the projection angle, i.e. the angle setting of the x-ray source relative to the object under examination, and, on the other, by the fan angle inside the x-ray beam, i.e. by the position of the detector pixel in the channel direction. The sinogram space accordingly represents the domain of the measured data, while the image space represents that of the image data. By means of a back projection, it is possible to pass from the sinogram space into the image space, i.e. from the measured data to the image data, and vice-versa by means of a forward projection from the image space into the sinogram space. The sinogram shows in schematic form that, after the calculation of the artificial measured value data, projection values are also present for the extended field of view, which corresponds to the two strips on the right and left edges of the sinogram.

Following this, the calculated projection data is modified in accordance with formula (1) by making use of the original measured data, from which a corrected projection data record data* results. The corrected projection data record data*, designated in the formulae as $p_{k,s,r}^{korr}$, is calculated by $$p_{k,s,r}^{korr} = \lambda_k \cdot p_{k,s,r}^{meas} + (1-\lambda_k) \cdot p_{k,s,r}^{proj} \quad \text{Formula (1)}$$

The mixing function $\lambda_k$ is calculated as follows:

$$\lambda_k = \begin{cases} 1 & m+z < k < n-z \\ \cos^2 \frac{\pi}{2} \frac{k-m}{n-k} & m \leq k \leq m+z \wedge n-z \leq k \leq n \\ 0 & k < m \wedge k > n \end{cases} \quad \text{Formula (2)}$$

where $$m = \frac{k_{eFOV} - k_{FOV}}{2} \text{ and } n = \frac{k_{eFOV} - k_{FOV}}{2};$$

m and n are fixed variables. The value of the mixing function $\lambda_k$ therefore depends only on k, the channel index.

$k_{FOV}$ designates the number of channels in the field of view, and $k_{eFOV}$ designates the number of channels in the field of view plus the virtual channels of the extended field of view. For example, $k_{FOV}$ may be 736, i.e. every detector line has 736 detector elements, and $k_{eFOV}$ 1000. In this case, the extended field of view would extend to both sides of the field of view by 132 detector elements.

z is a small fixed value, such as 20. It corresponds to a transition area, as explained hereinafter.

Figure 5:
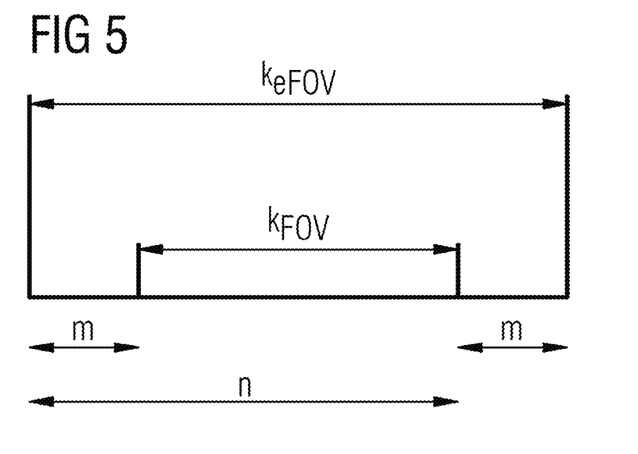
FIG. 5: an illustration for the understanding of the formulae (1) and (2).

FIG. 5 shows an illustration to assist in understanding the formulae (1) and (2). Shown here is the expansion of a detector line. Located in the middle is the number $k_{FOV}$ of the channels of the field of view. Connecting at the edge, on the right and left side, are in each case m virtual channels, which, together with the $k_{FOV}$ channels of the field of view, form the $k_{eFOV}$ channels of the field of view plus those of the extended field of view. Starting from the left edge of the line, the field of view begins after m channels and ends after n channels.

If the channel index k is smaller than m or greater than n (lower case from the formula (2)), then it corresponds to the channels of the extended field of view outside the field of view. For this case, the mixing function equals zero. This means that $p_{k,s,r}^{korr}$ is equal to $p_{k,s,r}^{proj}$. Outside the field of view, therefore, it is exclusively the calculated projection data $p_{k,s,r}^{proj}$ which is used for the image reconstruction.

If the channel index k lies between m and n, more precisely is removed by a distance interval of z from the borders m and n (upper case from the formula (2)), this then corresponds to the inner channels of the field of view. In this case, the mixing function is equal to one. This means that $p_{k,s,r}^{korr}$ is equal to $p_{k,s,r}^{meas}$. In the interior of the field of view, therefore, it is exclusively the measured projection data $p_{k,s,r}^{meas}$ which is used for the image reconstruction.

In the transition area, namely between m and m+z, as well as between n−z and n, the squared cosine function of the middle line of formula (2) has the effect of creating a soft transition between 1 and 0. In this area, therefore, a mixture is derived of the measured values $p_{k,s,r}^{meas}$ and the calculated values $p_{k,s,r}^{proj}$.

The measured data $p_{k,s,r}^{corr}$ corrected in accordance with formula (1) is used in the next step Recon, in order, with an inherently known algorithm, based, for example, on a Feldkamp-type algorithm, to reconstruct a CT image PIC of the object under examination within the extended field of view. This image PIC, which can be issued as a result image, shows the object under examination in the field of view and in the extended field of view, wherein, in particular in the extended field of view, a perceptible improvement in quality is achieved in comparison with the image PIC1.

In the step mask, as an alternative to the process described heretofore, in which a threshold value was used, in order, on the basis of the threshold value comparison, in binary form, to obtain a first CT value corresponding to the object under examination or a second CT value corresponding to areas which do not belong to the object under examination, the following procedure may be adopted:

Instead of a using a constant threshold value, a threshold value range is defined. Within this range, the CT values of the image PIC are blended from a maximum value to a minimum value, in order to determine the mask image PIC1 mask. As the maximum value, it is possible to set, for example, the CT value of water, i.e. 0 HU. As the minimum value, the CT value of air is suitable, i.e. −1000 HU. For the threshold value range, use may be made, for example of −600 HU to −400 HU. At and above −400 HU, the respective pixel is allocated as the maximum value, while below −600 HU the respective pixel is allocated as the minimum value. Between the two limit values, −600 HU to −400 HU, the CT values of the pixels are allocated in accordance with a linear or cos 2-shaped characteristic. Other characteristic forms and limit values are naturally also suitable, with which a continuous characteristic is attained between a maximum value and a minimum value.

As an alternative it is also possible for the mask image PIC1 mask to be produced as described heretofore, making use of only one threshold value, and then carrying out smoothing by a suitable filter function, such as, for example, a boxcar function or a generalized Gaussian filter. As a result of this, a continuous characteristic of CT values is also attained. The latter corresponds, in comparison with the binary mask image PIC1 mask, to a type of "fuzzy logic" approach.

The continuous characteristic of CT values in the extended measurement range, compared with the binary mask image PIC1 mask, corresponds to a more realistic image of the object under examination. As a result of this, too, the quality of the image PIC is enhanced.

The example embodiments described heretofore relate to the medical application of the invention. The invention can, however, be used outside the medical sector, for example in the examination of baggage, or the investigation of material.

The invention has been described heretofore on the basis of one exemplary embodiment. It is clearly understood that many changes and modifications are possible, without departing from the framework of the invention.

What is claimed is:

1. A method for the reconstruction of image data of an object under examination from measured data, wherein the measured data was acquired in a relative rotational movement between a radiation source of a computed tomography system and the object under examination, a delimited area between the radiation source and a detector representing a field of view, in respect of which the measured data can be acquired, and at least a part of the object under examination, during the acquisition of the measured data, was located at least for part of the time outside the field of view and other times the at least a part of the object under examination, during the acquisition of the measured data, was located at least part of the time inside the field of view, the method comprising:
reconstructing first image data from the measured data;
modifying the reconstructed first image data by use of a threshold value comparison;
processing the reconstructed modified first image data with a morphological filter;
projecting the filtered reconstructed modified first image data;
modifying the measured data by use of the projected filtered reconstructed modified first image data; and
reconstructing, from the modified measured data, second image data.

2. The method of claim 1, wherein, during the modifying the reconstructed first image data, pixel values of pixels are allocated a first or a second pixel value, depending on the threshold value comparison.

3. The method of claim 2, wherein, after the pixel value allocation, the first image data is subjected to a smoothing filtering process.

4. The method of claim 1, wherein during the modifying the reconstructed first image data, pixel values of pixels are allocated a pixel value from a plurality of available pixel values, depending on a comparison with a plurality of threshold values.

5. The method of claim 4, wherein, for the pixel value allocation, a continuous function is used, which represents an assignment between, in each case, a pixel value of the first image data and a pixel value from the plurality of pixel values available.

6. The method of claim 5, wherein, after the pixel value allocation, the first image data is subjected to a smoothing filtering process.

7. The method of claim 4, wherein, after the pixel value allocation, the first image data is subjected to a smoothing filtering process.

8. The method of claim 1, wherein, during the modifying the reconstructed first image data, pixel values of pixels are modified which form images of parts of the object under examination and are at least partly located outside the field of view during the measured data acquisition.

9. The method of claim 1, wherein, for at least one area outside the detector, the respective projection data is used for the reconstructing the second image data.

10. The method of claim 1, wherein, for at least one area of the detector, the respective measured data is used for the reconstructing the second image data.

11. The method of claim 1, wherein, for at least one area at the edge of the detector, a combination of the respective measured data and the respective projection data is used for the reconstructing the second image data.

12. The method of claim 1, wherein the reconstructing the first image data uses a method for image reconstruction in the extended field of view.

13. A calculation unit comprising:
a memory storing computer-readable instructions; and
a processor configured to execute the computer-readable instructions to,
reconstruct first image data from measured data, the measured data being acquired in a relative rotational movement between a radiation source of a computed tomography system and the object under examination, a delimited area between the radiation source and a detector representing a field of view, in respect of which the measured data can be acquired, and at least a part of the object under examination, during the acquisition of the measured data, was located at least for part of the time outside the field of view and other times the at least a part of the object under examination, during the acquisition of the measured data, was located at least part of the time inside the field of view,
modify the reconstructed first image data by use of a threshold value comparison,
process the reconstructed modified first image data with a morphological filter,
project the filtered reconstructed modified first image data,
modify the measured data by use of the projected filtered reconstructed modified first image data, and reconstruct, from the modified measured data, second image data.

14. A CT system comprising:
a radiation source configured to emit x-ray radiation;
a detector configured to detect the x-ray radiation;
a memory storing computer-readable instructions; and
a processor configured to execute the computer-readable instructions to,
reconstruct first image data from measured data, the measured data being acquired in a relative rotational movement between the radiation source and the object under examination, a delimited area between the radiation source and the detector representing a field of view, in respect of which the measured data can be acquired, and at least a part of the object under examination, during the acquisition of the measured data, was located at least for part of the time outside the field of view and other times the at least a part of the object under examination, during the acquisition of the measured data, was located at least part of the time inside the field of view, modify the reconstructed first image data by use of a threshold value comparison,
process the reconstructed modified first image data with a morphological filter,
project the filtered reconstructed modified first image data,
modify the measured data by use of the projected filtered reconstructed modified first image data, and
reconstruct, from the modified measured data, second image data.

15. A non-transitory computer-readable medium, when executed by a computer, configured to implement the method of claim 1.

16. The method of claim 1, wherein the modifying the measured data modifies the measured data further based on the measured data and a mixing function.

17. The method of claim 16, wherein the mixing function is a piecewise function.

18. The method of claim 17, wherein the mixing function is a function of a channel index of the detector.

* * * * *